(12) United States Patent
Koyama

(10) Patent No.: US 9,474,890 B2
(45) Date of Patent: Oct. 25, 2016

(54) LIQUID DISPENSING CIRCUIT

(75) Inventor: Shingo Koyama, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1023 days.

(21) Appl. No.: 13/611,163

(22) Filed: Sep. 12, 2012

(65) Prior Publication Data

US 2013/0006107 A1 Jan. 3, 2013

Related U.S. Application Data

(63) Continuation of application No. PCT/JP2011/055694, filed on Mar. 10, 2011.

(30) Foreign Application Priority Data

Mar. 26, 2010 (JP) .................. 2010-073415

(51) Int. Cl.
*A61M 39/22* (2006.01)
*F16K 39/06* (2006.01)
*A61M 5/00* (2006.01)
*A61B 6/00* (2006.01)

(52) U.S. Cl.
CPC ........... *A61M 39/223* (2013.01); *A61M 5/007* (2013.01); *F16K 39/06* (2013.01); *A61B 6/481* (2013.01)

(58) Field of Classification Search
CPC .... A61M 39/223; A61M 5/007; F16K 39/06
See application file for complete search history.

(56) References Cited

U.S. PATENT DOCUMENTS

| 3,678,960 A | 7/1972 | Leibinsohn |
| 5,466,228 A | 11/1995 | Evans |
| 5,916,201 A | 6/1999 | Wilson, Jr. et al. |
| 8,356,629 B2 * | 1/2013 | Koyama ............. A61M 39/223 137/625.19 |
| 2003/0125673 A1 | 7/2003 | Houde et al. |
| 2003/0181850 A1 | 9/2003 | Diamond et al. |
| 2005/0043668 A1 | 2/2005 | Yuki |

(Continued)

FOREIGN PATENT DOCUMENTS

| AU | 2006-241307 A1 | 6/2007 |
| CN | 1984690 A | 6/2007 |

(Continued)

OTHER PUBLICATIONS

Japanese Office Action issued on Jun. 2, 2015, by the Japanese Patent Office in corresponding Japanese Patent Application No. 2012-506934. (6 pgs).

(Continued)

*Primary Examiner* — Amanda Lauritzen Moher
(74) *Attorney, Agent, or Firm* — Buchanan Ingersoll & Rooney PC

(57) ABSTRACT

A liquid dispensing circuit is provided with: a multi-way cock; a first line; a second line; a third line; a fourth line; a fifth line; and a casing which houses some of the above. When a cock in the multi-way cock is situated in a priming position, a distal opening in a second part of a first flow channel communicates with a first port, and a distal opening in a third part communicates with a second port; thus, the first port and the second port are in an open state wherein the ports are connected to each other via the first flow channel, whereas a third port, a fourth port, and a sixth port are in an open state wherein the ports are connected to one another via a second flow channel.

17 Claims, 12 Drawing Sheets

(56) References Cited

U.S. PATENT DOCUMENTS

| | | |
|---|---|---|
| 2005/0085682 A1 | 4/2005 | Sasaki et al. |
| 2006/0161113 A1 | 7/2006 | Denolly |
| 2009/0131862 A1 | 5/2009 | Buck et al. |
| 2010/0030074 A1 | 2/2010 | Imai et al. |
| 2010/0191106 A1 | 7/2010 | Koyama |

FOREIGN PATENT DOCUMENTS

| | | |
|---|---|---|
| EP | 2 078 536 A1 | 7/2009 |
| EP | 2 158 934 A1 | 3/2010 |
| JO | 2002-306609 A | 10/2002 |
| JP | 9-108360 A | 4/1997 |
| JP | 11-503926 A | 4/1999 |
| JP | 2006-510448 A | 3/2006 |
| JP | 2006-519053 A | 8/2006 |
| JP | 2007-143830 A | 6/2007 |
| JP | 2008-506428 A | 3/2008 |
| WO | 03/041788 A1 | 5/2003 |
| WO | 2004/075972 A1 | 9/2004 |
| WO | 2008/047699 A1 | 4/2008 |
| WO | WO 2008/155938 A1 | 12/2008 |

OTHER PUBLICATIONS

Office Action issued on Jan. 10, 2014, by the Chinese Patent Office in corresponding Chinese Patent Application No. 201180015730.3. (6 pages).

International Search Report (PCT/ISA/210) Issued on May 10, 2011, by the Japanese Patent Office as the International Searching Authority for International Application No. PCT/JP2011/055694.

The extended European Search Report issued on Jul. 21, 2014, by the European Patent Office in European Patent Application No. 11759217.0 (5 pages).

* cited by examiner

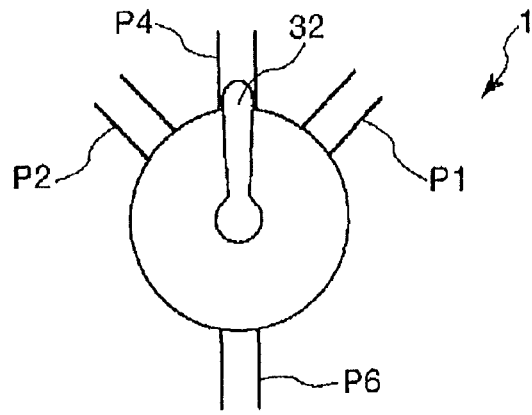
FIG. 12(a)
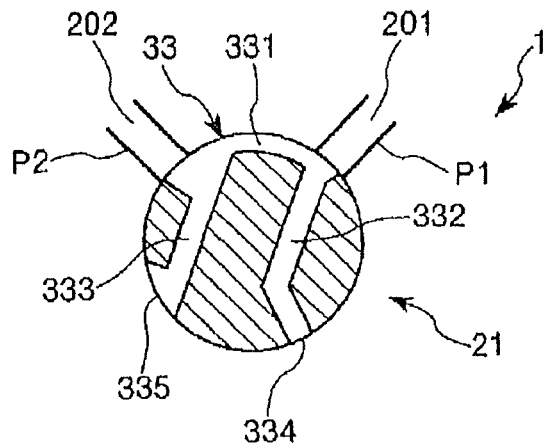
FIG. 12(b)
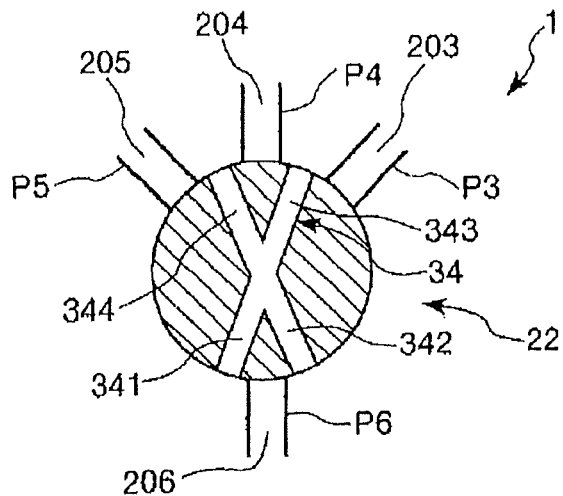
FIG. 12(c)
FIG. 12

LIQUID DISPENSING CIRCUIT

CROSS-REFERENCES TO RELATED APPLICATIONS

This application is a continuation of International Application No. PCT/JP2011/055694 filed on Mar. 10, 2011, and claims priority to Japanese Patent Application JP2010-073415 filed in the Japanese Patent Office on Mar. 26, 2010, the entire content of both of which is incorporated herein by reference.

TECHNICAL FIELD

The present invention generally relates to a liquid dispensing circuit.

BACKGROUND DISCUSSION

At the time of treating coronary arterial stenosis, a minimally invasive treatment using a catheter has been used. Performing this surgical operation involves injecting a radiopaque material for the purpose of checking the position of the catheter and/or the state of the stenosed part. In addition, flushing with physiological saline is performed for securing the contrast of an image as required. Furthermore, a pressure monitor for measuring (detecting) the arterial pressure and displaying the arterial pressure is always connected to this circuit, so as to check the arterial pressure, and the pressure monitor is disconnected at the time of injecting the radiopaque material or physiological saline.

To carry out these operations, the flow channel in the circuit has to be changed over. As a way of changing over the flow channel, conventionally, a three-in-series type three-way cock has been used.

In the case of the three-in-series type three-way cock, however, there are three cocks and the three cocks have to be operated, so that the operations are intricate and it is impossible to achieve speedy changeover of the flow channel.

A device described in Japanese Patent Laid-open No. Hei 9-108360 describes an arrangement for simplifying these operations, but the device has a problem that only changeover between a radiopaque material route (flow channel) and a pressure monitor route can be performed, and it is impossible to make a changeover to a physiological saline route. Besides, an addition of a physiological saline route is difficult to realize, since such an addition complicates the mechanism.

SUMMARY

According to one aspect, a liquid dispensing circuit comprises: a multi-way cock comprised of a tubular cock body and a trunk part, with the tubular cock body possessing a lumen, and the trunk part being rotatably positioned in the lumen of the tubular cock body to rotate at least from a first rotational position to a second rotational position, wherein the first and second positions are different. The tubular cock body includes opposite axial ends and a circumferential outer surface between the axial ends, with the tubular cock body including a plurality of ports projecting outwardly away from the circumferential outer surface of the tubular cock body, and the plurality of ports comprising a first port, a second port, a third port, a fourth port, a fifth port and a sixth port. The first port and the second port each possess a lumen having one end opening to the lumen in the tubular cock body and an opposite end opening outside the tubular cock body. The third port, the fourth port, the fifth port and the sixth port each possess a lumen having one end opening to the lumen in the tubular cock body and an opposite end opening outside the tubular cock body. The trunk part includes a first flow channel configured so that in the first rotational position of the trunk part, one portion of the first flow channel opens to the one end of the first port while another portion of the first flow channel opens to the one end of the second port so that the first and second ports fluidly communicate with one another by way of the first flow channel, and so that in the second rotational position of the trunk part, the other portion of the first flow channel is spaced from the one end of the second port, and the first and second ports are not in fluid communication with one another by way of the first flow channel. The one portion of the first flow channel and the other portion of the first flow channel are circumferentially spaced from one another, and the trunk part also includes a second flow channel separate from the first flow channel and axially spaced from the first flow channel. The second flow channel is configured so that: in the second rotational position of the trunk part, a first portion of the second flow channel opens to the one end of the third port, a second portion of the second flow channel opens to the one end of the fourth port and a third portion of the second flow channel opens to the one end of the sixth port so that the third, fourth and sixth ports fluidly communicate with one another by way of the second flow channel; in the first rotational position of the trunk part, the first portion of the second flow channel opens to the one end of the third port, the second portion of the second flow channel opens to the one end of the fourth port and the third portion of the second flow channel opens to the one end of the sixth port so that the third, fourth and sixth ports fluidly communicate with one another by way of the second flow channel. The first portion of the second flow channel, the second portion of the second flow channel and the third portion of the second flow channel are circumferentially spaced from one another. The circuit also includes a plurality of tubes each possessing a lumen and connected to a different one of the plurality of ports so that the lumen in each tube is in fluid communication with the respective port. The liquid dispensing circuit allows a priming operation to be performed relatively easily and assuredly, and permits complicated flow channel changeover operations to be carried out rather easily and speedily.

According to another aspect, a liquid dispensing circuit comprises: a multi-way cock comprised of a cock body having a tubular part, with the tubular part of the cock body including axially side-by-side first and second portions which each possesses an outer circumference, wherein the first portion of the cock body includes a first port and a second port both positioned at the outer circumference of the first portion in circumferentially side-by-side relation, and wherein the second portion of the cock body includes a third port, a fourth port, a fifth port, and a sixth port sequentially positioned side-by-side about the outer circumference of the second portion. The cock also includes a trunk part turnably positioned in the tubular part, with the trunk part provided with a first flow channel to communicate the first port and the second port, the trunk part also being provided with a second flow channel to communicate the third port, the fourth port, the fifth port and the sixth port in a predetermined combination. A second line has one end portion connected to the second port and an opposite end portion configured to be connected to blood pressure detection means for detecting blood pressure of a patient, a third line has one end portion connected to the third port and an opposite end portion configured to be connected to a container containing physiological saline, a fourth line has one end portion connected to the fourth port and an opposite end portion configured to be connected to a flow channel communicating with a blood vessel of the patient; a first line connects the first port and the fourth line, and a fifth line has one end portion connected to the fifth port and an opposite end portion configured to be connected to a container containing a radiopaque material. The sixth port is configured to be connected to liquid feeding means for feeding a liquid from one of the first line, the second line, the third line, the fourth line and the fifth line to a different one of the first line, the second line, the third line, the fourth line and the fifth line through the multi-way cock. The cock is movable to shift from a priming position to effect priming before use, a radiopaque material dispensing position to dispense the radiopaque material to the patient, a physiological saline dispensing position to dispense the physiological saline to the patient, and a blood pressure detection position to detect the blood pressure of the patient by the pressure detection means. When the cock is situated in the priming position, the first port and the second port communicate with each other through the first flow channel, while at the same time the third port, the fourth port and the sixth port communicate with one another through the second flow channel.

The first flow channel preferably includes: a first part provided in an outer circumferential surface of the trunk part and extending in the circumferential direction of the trunk part; a second part extending from one end portion of the first part, penetrating the trunk part and forming a distal opening at the outer circumferential surface of the trunk part; and a third part extending from the other end portion of the first part, penetrating the trunk part and forming a distal opening at the outer circumferential surface of the trunk part.

The liquid dispensing circuit is preferably so configured that when the cock is situated in the priming position, the distal opening of the second part communicates with the first port, and the distal opening of the third part communicates with the second port, whereby the first port and the second port are made to communicate with each other through the first flow channel.

The liquid dispensing circuit is preferably configured so that when the cock is situated in the blood pressure detection position, the first part communicates with both the first port and the second port, whereby the first port and the second port are set in an open state wherein these ports communicate with each other through the first flow channel, whereas the third port, the fourth port, the fifth port and the sixth port are each set in a closed state.

The liquid dispensing circuit is preferably so configured that when the cock is situated in the blood pressure detection position, the first port and the second port are set in an open state wherein these ports communicate with each other through the first flow channel, whereas the third port, the fourth port, the fifth port and the sixth port are each set in a closed state.

The liquid dispensing circuit is preferably also configured that when the cock is situated in the radiopaque material dispensing position, the first port and the second port are each set in a closed state, whereas the fourth port and the fifth port and the sixth port are set in an open state wherein these ports communicate with one another through the second flow channel.

When the cock is situated in the physiological saline dispensing position, the first port and the second port are preferably each set in a closed state, whereas the third port, the fourth port and the sixth port are preferably set in an open state wherein these ports communicate with one another through the second flow channel.

The radiopaque material dispensing position, the physiological saline dispensing position and the blood pressure detection position are preferably concentratedly provided within the range of a central angle of not more than 120°, and the priming position is provided outside the range.

The multi-way cock can have positioning means by which the range of turning of the cock relative to the tubular part is restricted within such a range that the cock can be moved to the radiopaque material dispensing position, the physiological saline dispensing position, and the blood pressure detection position. The liquid dispensing circuit is preferably so configured that when the positioning means is not functioning, the cock can be moved to the priming position.

The liquid dispensing circuit is also preferably configured so that once the cock is moved from a first region wherein the priming position is provided into a second region wherein the radiopaque material dispensing position, the physiological saline dispensing position and the blood pressure detection position are provided, the cock cannot be returned into the first region.

A method of dispensing liquids comprises: positioning a cock in a priming position, wherein the cock comprises a tubular cock body possessing a lumen, the tubular cock body including a plurality of ports each possessing a lumen and opening to the lumen in the tubular cock body, with the plurality of ports comprising a first port, a second port, a third port, a fourth port, a fifth port and a sixth port; a trunk part rotatably positioned in the lumen of the tubular cock body and wherein the trunk part includes a first flow channel and a second flow channel separate from the first flow channel. The method also involves priming the cock by causing physiological saline to flow, while the cock is in the priming position, from a source of physiological saline to the third port, through the second flow channel and into the sixth port in that order, and then causing the physiological saline which has flown into the sixth port to flow, while the cock is in the priming position, through the first flow channel, through the first port, through the second part and through the fourth port. The method additionally includes rotating the trunk body relative to the tubular cock body to position the cock in a radiopaque material dispensing position in which the first and second ports are not in fluid communication by the first flow channel, and drawing radiopaque material from a source of radiopaque material while the cock is in the radiopaque material dispensing position to cause the radiopaque material to flow from the source of radiopaque material through the fifth port, through the second flow channel and into the sixth port in that order, and then causing the radiopaque material which has flown into the sixth port to flow through the second flow channel and through the fourth port. The method further includes rotating the trunk body relative to the tubular cock body to position the cock in a blood pressure detection position in which the third port, the fourth port, the fifth port and the sixth port are not in fluid communication with each other, and allowing blood of a patient to flow, while the cock is in the blood pressure detection position, from the patient through the first port, through the first flow channel, through the second port and to a blood pressure monitor which measures pressure of the patient's blood.

BRIEF DESCRIPTION OF THE DRAWINGS

FIGS. 12(a), 12(b) and 12(c) are cross-sectional views somewhat schematically illustrating a flow channel changeover pattern in the multi-way cock shown in FIG. 5.

DETAILED DESCRIPTION

Figure 1:
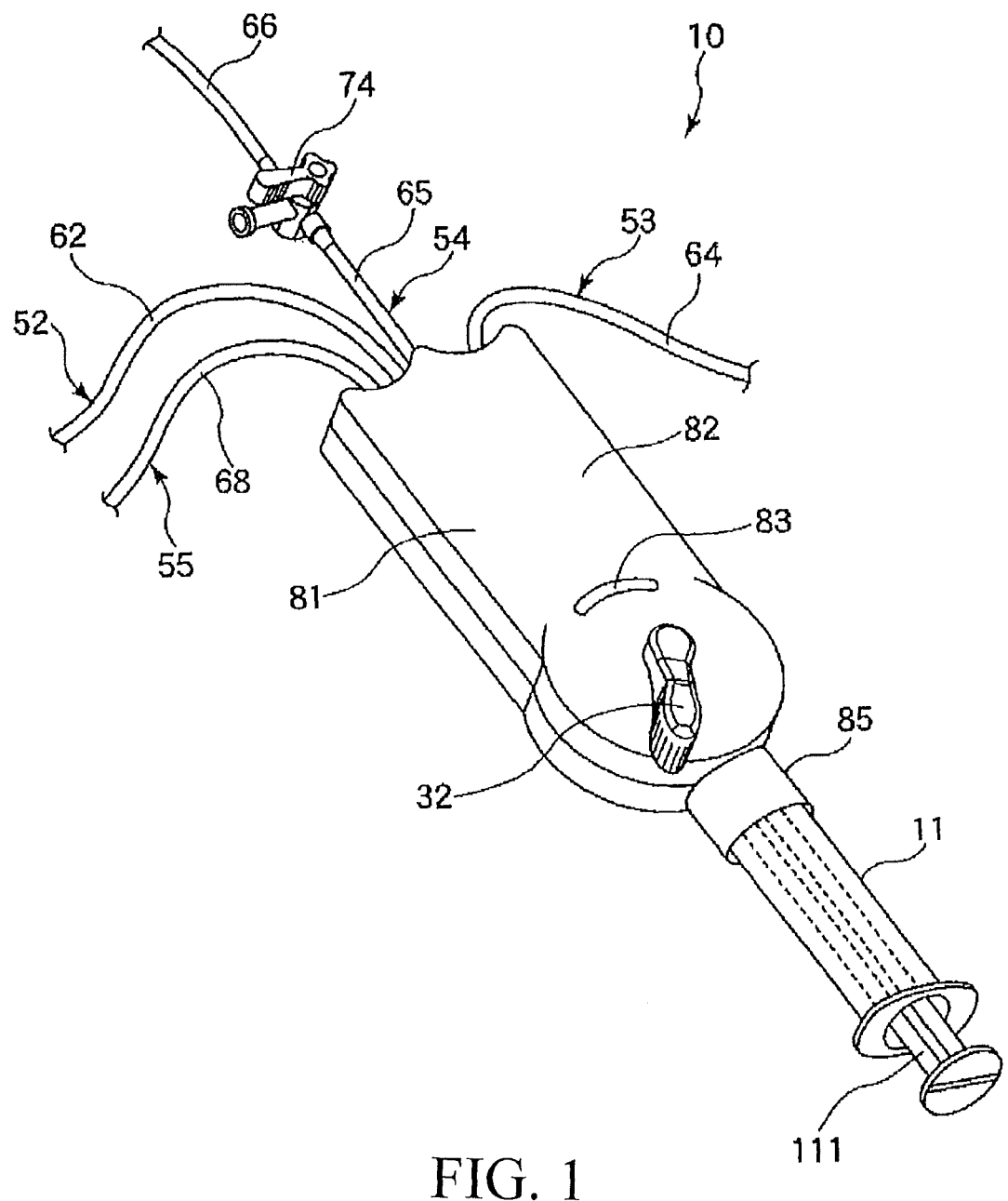
FIG. 1 is a perspective view of an embodiment of a liquid dispensing circuit representing one example of the liquid dispensing circuit disclosed here.
Figure 2:
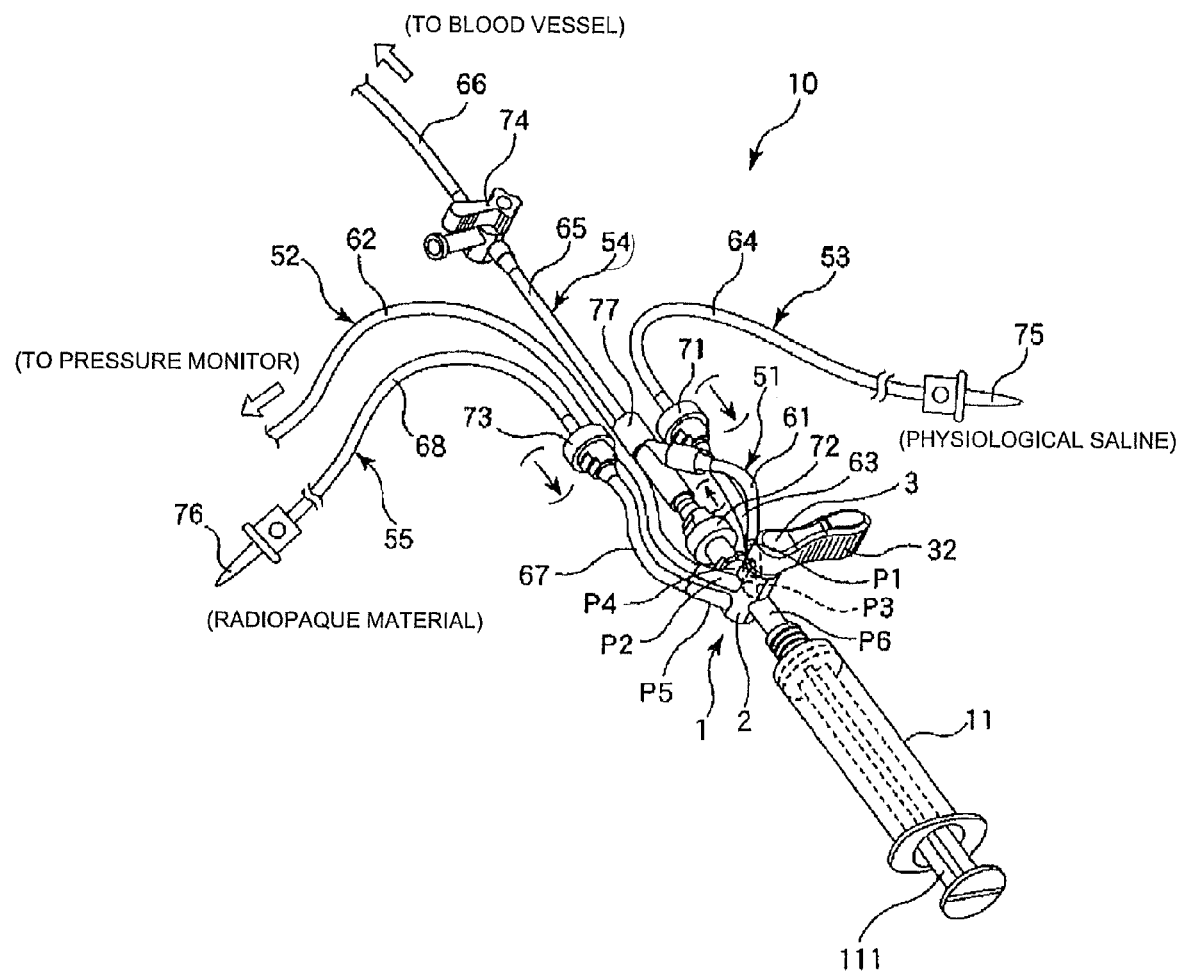
FIG. 2 is a perspective view of the liquid dispensing circuit shown in FIG. 1, showing a state in which a casing has been detached.
Figure 5:
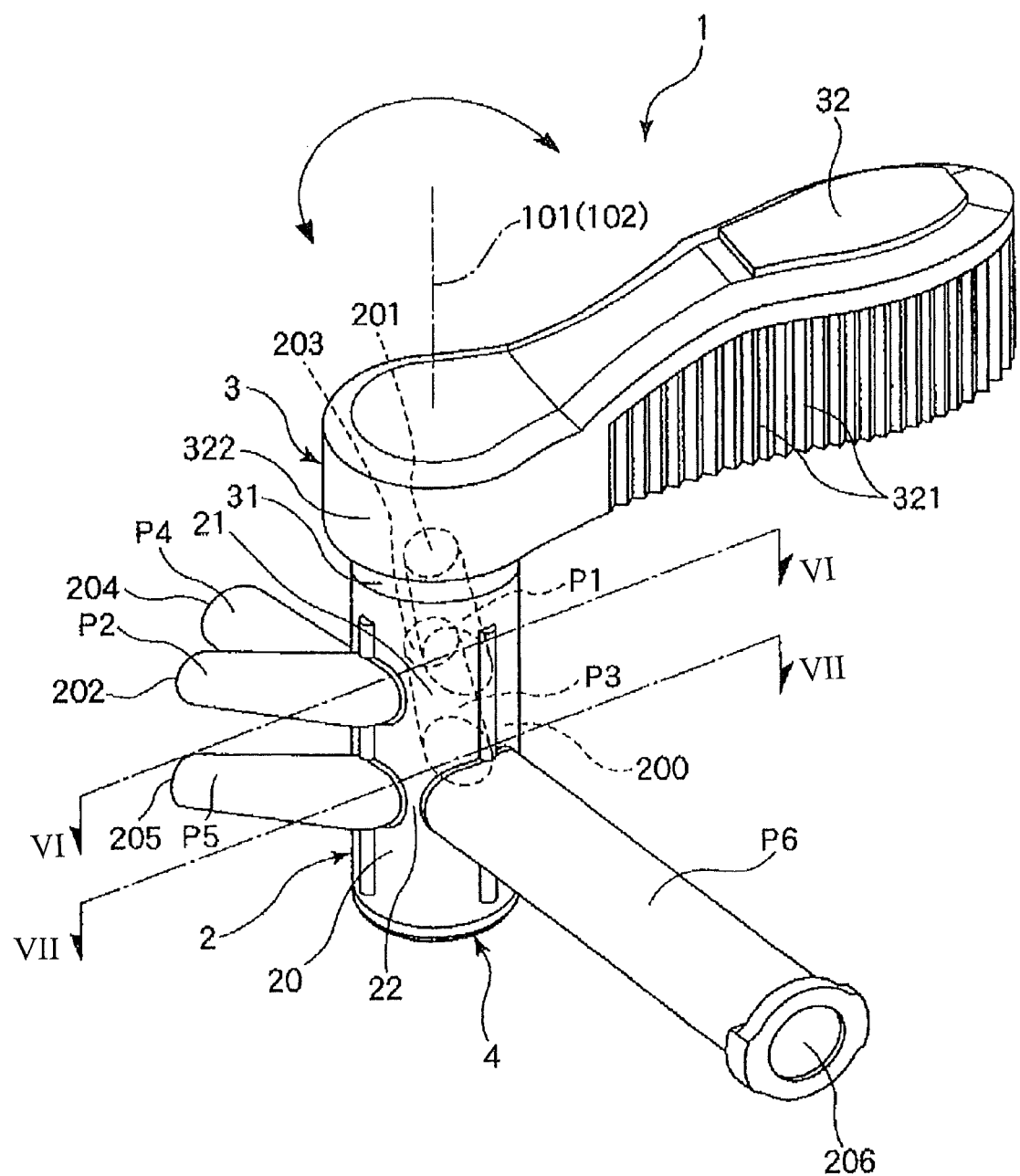
FIG. 5 is a perspective view of a multi-way cock in the liquid dispensing circuit shown in FIG. 1.
Figure 8A:
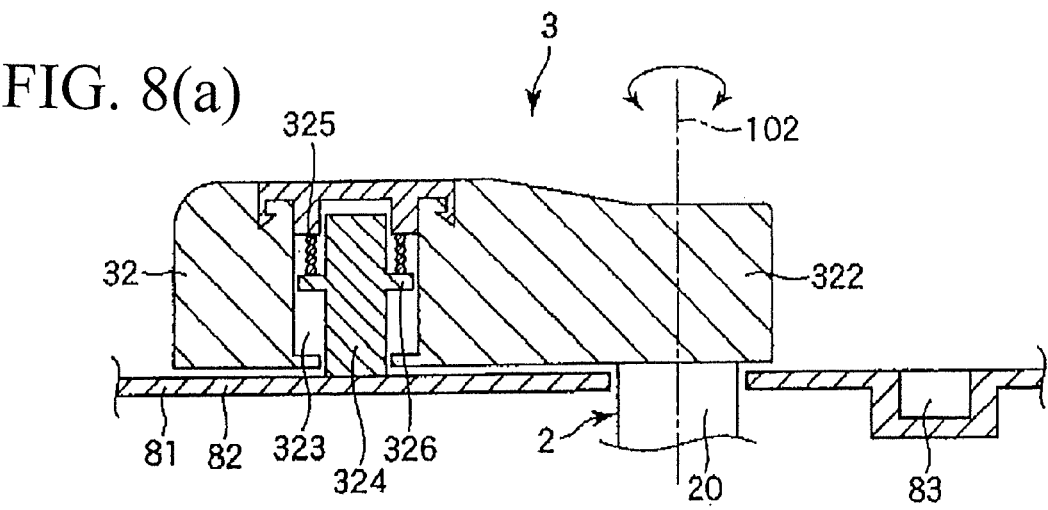
FIGS. 8(a) and 8(b) are cross-sectional views of a wall portion of the casing and a lever of the multi-way cock in the liquid dispensing circuit shown in FIG. 1.
Figure 8B:
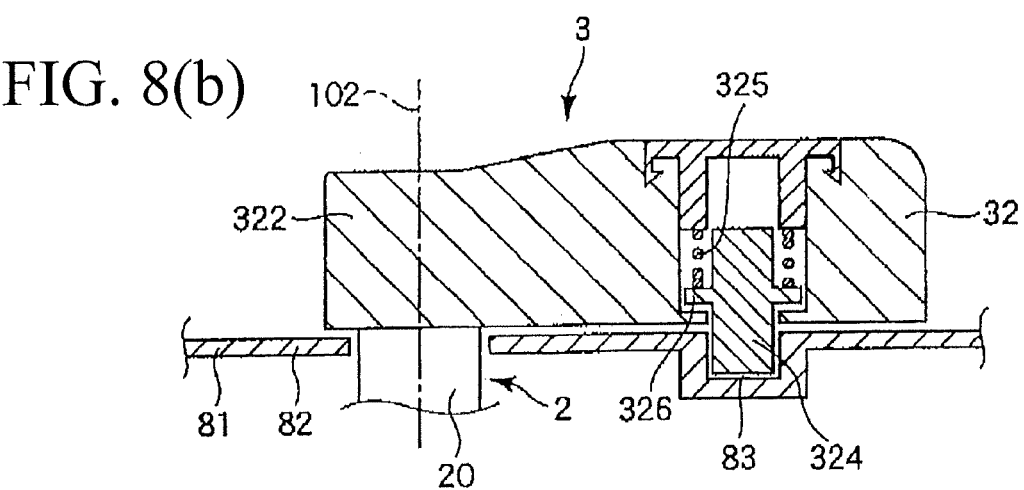

Set forth below is a detailed description of a liquid dispensing circuit illustrated in the accompanying drawings representing one example of the liquid dispensing circuit disclosed here. In the following description, the upper side in FIGS. 1, 5 and 8 is referred to as "upper" or "upper end," while the lower side is referred to as "lower" or "lower end."

The liquid dispensing circuit 10 shown in these figures is, for example, a circuit (device) which is used at the time of treating coronary arterial stenosis for dispensing (injecting) physiological saline or a radiopaque material into a patient (a person for whom the circuit is to be used).

As shown in FIGS. 1 to 4, the liquid dispensing circuit 10 comprises: a multi-way cock representing an example of a flow channel changeover means 1 which includes a first port P1, a second port P2, a third port P3, a fourth port P4, a fifth port P5, a sixth port P6 and a lever 32; a first line 51; a second line 52; a third line 53; a fourth line 54; a fifth line 55; and a casing (housing) 81 for housing some (most) of these members. The casing 81 has a box-like shape which is flat on its top and bottom surfaces and possesses rounded corner portions. In addition, the multi-way cock 1 is fixedly disposed inside the casing 81 so that its lever 32 is situated on the outer side (upper side) of a wall portion 82, on the upper side in FIG. 1, of the casing 81. The multi-way cock 1 and the casing 81 will be described in detail later.

The second line 52 is a line through which to connect the second port P2 and a pressure sensor (an example of a blood pressure detection means) for detecting the blood pressure of a patient, and includes a tube 61.

The proximal end of the tube 62 is connected to the second port P2. The tube 62 is, at a distal end thereof from an intermediate portion thereof, disposed on (led out to) the outside of the casing 81, and the distal end of the tube 62 is connected to the pressure sensor. For example, arterial pressure (blood pressure in the coronary artery) or the like is measured (detected) by the pressure sensor, and the measurement result (detection result) is displayed on a monitor which is an example of display means for displaying the result.

The third line 53 is a line through which to connect the third port P3 and a container (vial or the like) (not shown) reserving physiological saline, and includes tubes 63, 64, a check valve 71 and an air vent integral type bottle needle 75. In the configuration shown, the check valve 71 used is one which permits tubes to be connected (coupled) to both end portions of the check valve.

The proximal end of the tube 63 is connected to the third port P3, the distal end of the tube 63 is connected to one end side of the check valve 71, and proximal end of the tube 64 is connected to the other end side of the check valve 71. The tube 64 is, at a distal end thereof from an intermediate portion thereof, disposed on the outside of the casing 81, and the air vent integral type bottle needle 75 is connected to the distal end of the tube 64. The bottle needle 75 is connected to the container reserving the physiological saline.

In addition, the check valve 71 permits a liquid (fluid) to flow through the check valve 71 from the side of the bottle needle 75 (physiological saline) to the side of the third port P3 (multi-way cock 1) and to inhibit the liquid from flowing through the check valve 71 in the reverse direction. The parenthetical arrows in the vicinities of the check valves 71 to 73 in FIG. 2 indicate the directions in which liquid can flow.

The fourth line 54 is a line through which to connect the fourth port P4 and a tube (flow channel) communicating with a blood vessel of the patient, and includes the check valve 72, a branched connector 77 composed of a three-way branch pipe (T-pipe, Y-pipe, non-right angled T-pipe or the like), tubes 65 and 66, and three-way cock (drug dispensing cock) 74. In the configuration shown, the check valve 72 used is one which is provided at one of its end portions with a female-type Luer taper, and is provided at its other end portion with a male-type Luer taper. In addition, a port of the branched connector 77 on the side for connection with the check valve 72 is formed with a female-type Luer taper, and the remaining two ports of the branched connector 77 are tapered in shape so as to permit tubes to be connected thereto.

Specifically, the female-type Luer taper on one end side of the check valve 72 is connected to the fourth port P4, the male-type Luer taper on the other end side of the check valve 72 is connected to a female-type Luer taper formed at one port of the other two ports of the branched connector 77, and the proximal end of the tube 65 is connected to the other port of the branched connector 77. This tube 65 is, at the distal end thereof from an intermediate portion thereof, disposed on the outside of the casing 81, and the distal end of the tube 65 is connected to one of the ports of the three-way cock (drug dispensing cock) 74. The proximal end of the tube 66 is connected to the other one port of the three-way cock 74, and the distal end of the tube 66 is to be connected to the proximal end of a catheter (tube). The distal end of the catheter is inserted into a patient's blood vessel, and extends through the blood vessel to reach the vicinity of a stenosed part (target part) of a coronary artery.

In addition, the check valve 72 is provided to permit a liquid (fluid) to flow through the check valve 72 from the fourth port P4 (multi-way cock 1) side to the branched connector 77 (patient) side and to inhibit the liquid from flowing in the reverse direction.

The port (remaining port) of the three ports of the three-way cock 77 which is not connected to anything is used, for example, in the case of dispensing a drug such as nitroglycerin or in the case of drawing blood (arterial blood).

The first line 51 is a line through which to connect the first port P1 and the fourth line, and includes a tube 61.

One end (the proximal end) of the tube 61 is connected (coupled) to the first port P1, and the other end (the distal end) of the tube 61 is connected to one of the ports of the branched connector 77.

The fifth line 55 is a line through which to connect the fifth port P5 and a container (bag, bottle or the like) in which is contained or reserved a radiopaque material, and includes tubes 67 and 68, a check valve 73 and an air vent integral type bottle needle 76. In the configuration shown, the check valve 73 used is one which permits tubes to be connected to both end portions thereof.

The proximal end of the tube 67 is connected to the fifth port P5, the distal end of the tube 67 is connected to one end side of the check valve 73, and the proximal end of the tube 68 is connected to the other end side of the check valve 73. This tube 68 is, at the distal end thereof from an intermediate portion thereof, disposed on the outside of the casing 81, and the air vent integral type bottle needle 76 is connected to the distal end of the tube 68. The bottle needle 76 is to be connected to the container (not shown) reserving the radiopaque material.

In addition, the check valve 73 is provided to permit a liquid to flow check valve 73 from the bottle needle 76 (radiopaque material) side to the fifth port P5 (multi-way cock 1) side and to inhibit the liquid from flowing in the reverse direction.

The bottle needle 75 and the bottle needle 76 are, or the tube 64 and the tube 68 are, preferably colored in different colors. This makes it possible to prevent misconnection of the bottle needles 75, 76. In other words, connection of the bottle needle 75 to the container reserving the physiological saline therein and connection of the bottle needle 76 to the container reserving the radiopaque material therein can be carried out in an assured manner.

The sixth port P6 is to be connected to liquid feeding means for feeding a liquid from one line of the first to fifth lines 51 to 55 to another line through the multi-way cock 1. Specifically, the sixth port P6 is connected to a syringe 11 provided as the liquid feeding means, either directly or via a tube (flow channel) or the like.

In the configuration shown, the syringe 11 is connected directly to the sixth port P6. In this case, that portion of the casing 81 which corresponds to the sixth port P6 is formed with a tube body 85 for holding an outer tube of the syringe 11, and a distal end portion of the sixth port P6 is situated inside the tube body 85. This helps ensure that when the syringe 11 is connected to the sixth port P6, the outer tube of the syringe 11 is fitted into the tube body 85, whereby the syringe 11 is held.

Figure 6:
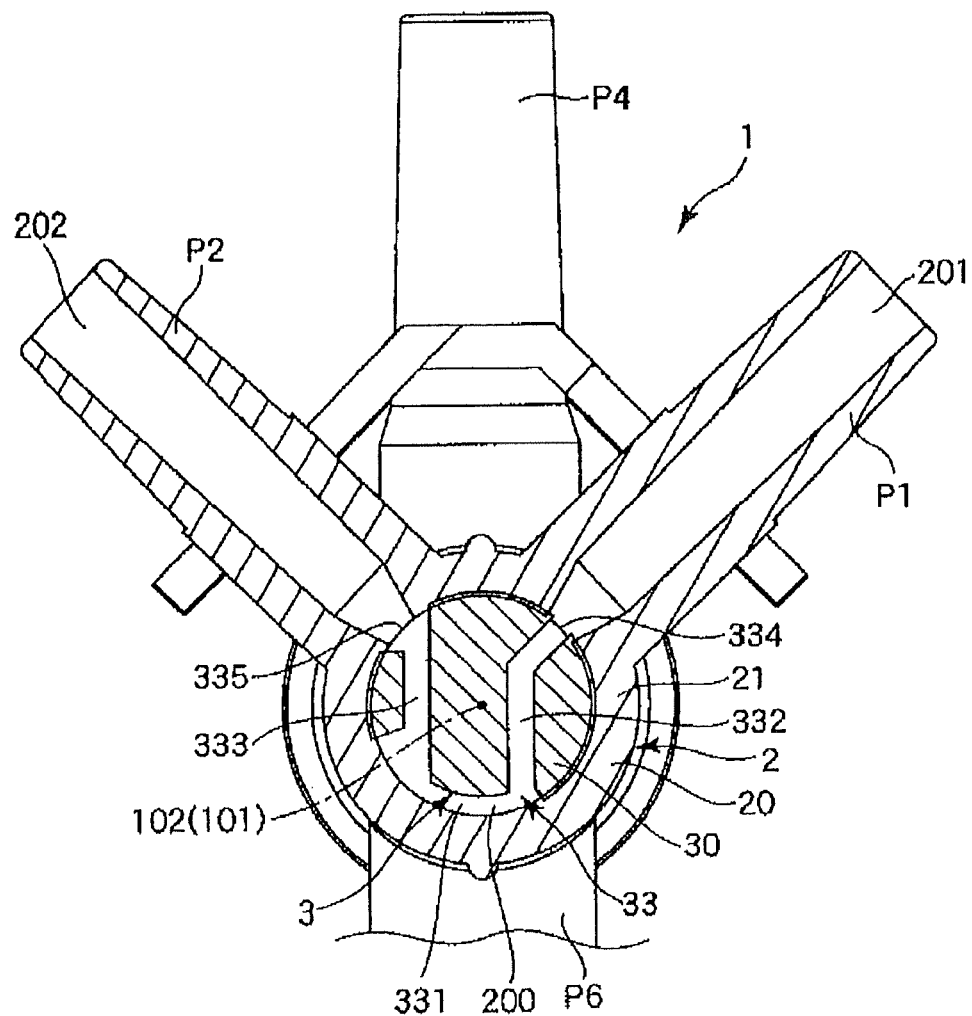
FIG. 6 is a cross-sectional view of the multi-way cock shown in FIG. 5, taken along the section line VI-VI in FIG. 5.
Figure 7:
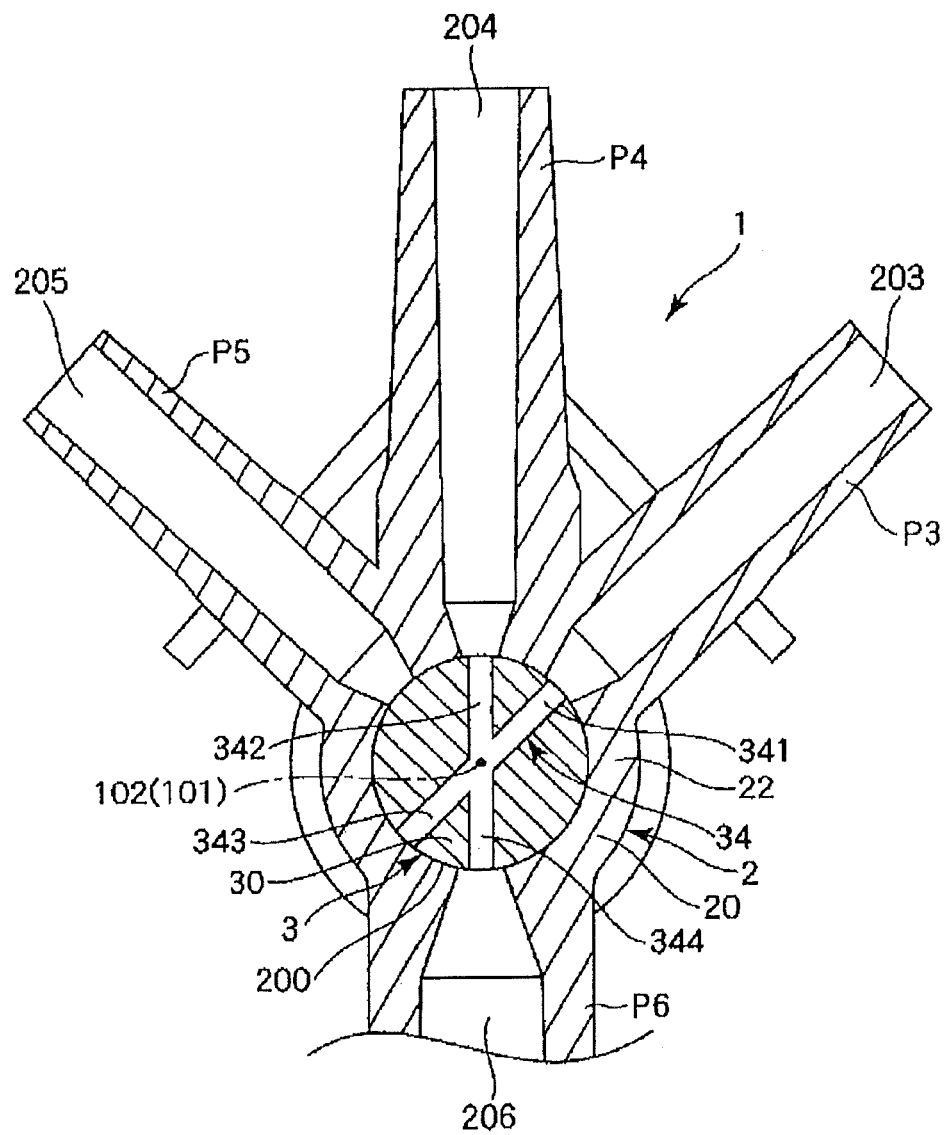
FIG. 7 is a cross-sectional view of the multi-way cock shown in FIG. 5, taken along the section line VII-VII in FIG. 5.

Now, the multi-way cock 1 will be described. As shown in FIGS. 5 to 7, the multi-way cock (flow channel change-over means) 1 is a two-stage type multi-way cock, and includes a cock body 2, a cock 3, and a cover 4.

The cock body 2 is comprised of a thick-walled hollow cylindrical part (tubular part) 20. The hollow cylindrical part 20 has a first portion 21 and a second portion 22 which are provided side by side along an axis (center axis) 101. In the configuration shown, the first portion 21 is disposed on the upper side (upper stage), and the second portion 22 is disposed on the lower side (lower stage) so that the first portion 21 is positioned above the second portion 22. A configuration may also be adopted in which, the first portion 21 is disposed on the lower side and the second portion 22 on the upper side so that the second portion 21 is positioned above the first portion 22.

At the outer circumference of the first portion 21, the first port P1 and the second port P2 having tubular bodies (branch tubes) projecting outward in radial directions (directions perpendicular to the axis 101) at a predetermined angle therebetween are provided (formed) side by side along the circumferential direction. In addition, flow channels 201 and 202 formed inside the first port P1 and the second port P2 communicate with a lumen 200 of the hollow cylindrical part 20 at an equal height position. That is the central axes of the flow channels 201, 202 lie in a common horizontal plane.

The angular interval between the first port P1 and the second port P2 is 90° in the configuration shown by way of example, but the angular interval is not limited to this value.

At the outer circumference of the second portion 22, the third port P3, the fourth port P4, the fifth port P5 and the sixth port P6 having tubular bodies (branch tubes) projecting outward in radial directions (directions perpendicular to the axis 101) at predetermined angles therebetween are sequentially provided (formed) side by side along the circumferential direction. Specifically, the third port P3, the fourth port P4, the fifth port P5 and the sixth port P6 are disposed in this order and in such a manner that the third port P3 and the first port P1 project in the same direction while the fifth port P5 and the second port P2 project in the same direction. In plan view (as viewed from the upper side in FIG. 5), the third port P3 and the first port P1 coincide (overlap) with each other, while the fifth port P5 and the second port P2 coincide (overlap) with each other. That is, the central axes of the third port P3 and the first port P1 lie in a common vertical plane, while the central axes of the fifth port P5 and the second port P2 lie in a common vertical plane (with the cock body 2 positioned upright as shown in FIG. 5). In addition, flow channels 203, 204, 205 and 206 formed inside the third to sixth ports P3 to P6 communicate with the lumen 200 of the hollow cylindrical part 20 at an equal height position. That is the central axes of the flow channels 203, 204, 205, 206 lie in a common horizontal plane (with the cock body 2 positioned upright as shown in FIG. 5).

The angular interval between the third port P3 and the fourth port P4 and the angular interval between the fourth port P4 and the fifth port P5 are each 45° in the configuration shown, but the angular intervals are not limited to this value. The angular interval between the sixth port P6 and the third port P3 and the angular interval between the fifth port P5 and the sixth port P6 are each 135° in the configuration shown, but the angular intervals are not limited to this value.

In addition, distal end portions of the first to third ports P1 to P3 and the fifth port P5 gradually decrease in outside diameter toward the distal end. In other words, the distal end portions possess gradually decreasing outside diameter portions (tapered portions). This helps enable relatively easy connection (coupling) of tubes or the like to the distal end portions of the first to third ports P1 to P3 and the fifth port P5.

The distal end portion of the fourth port P4 includes a male-type Luer taper. This helps enable relatively easy connection of a female-type Luer taper or the like to the distal end portion of the fourth port P4.

In addition, the distal end portion of the sixth port P6 is formed with a female-type Luer taper. This enables easy connection of a syringe or the like to the distal end portion of the sixth port P6.

The cock 3 has a trunk part (insertion part) 30, a lever mounting part 31, and a lever (operating part) 32. With a turning operation applied to the cock 3, namely, with the cock 3 turned (rotated in a forward direction or a reverse direction) relative to the cock body 2, open/closed states of the first to sixth ports P1 to P6 provided in the first portion 21 and the second portion 22 are selected.

The trunk part 30 is solid-cylindrical in shape, and it is turnably positioned (fitted) in the lumen 200 of the hollow cylindrical part 20 in a gas-tight or liquid-tight manner. Therefore, the outside diameter of the trunk part 30 in the condition where the cock 3 has been drawn out of the hollow cylindrical part 20 is preferably a little greater, for example greater by about 1 to 6%, than the inside diameter of the hollow cylindrical part 20.

That portion of the trunk part 30 which corresponds to the first portion 21 is formed therein with a first flow channel 33 through which the first port P1 and the second port P2 formed in the first portion 21 communicate with each other (in the case where the number of ports is three or more, the ports communicate with one another in a predetermined combination). The state in which a port is communicating with another port will be referred to as an "open state," while the state in which a port is not communicating with any other port will be referred to as a "closed state."

The first flow channel 33 is so formed that both the first port P1 and the second port P2 can simultaneously be set into an open state or a closed state (in the case where the number of ports is three or more, the first flow channel 33 is so formed that predetermined two of the ports can be simultaneously set into an open state or a closed state).

Specifically, the first flow channel 33 includes: a first part 331 which is formed (provided) the outer circumferential surface of the trunk part 30 (the first part 331 opens outward) and extends in the circumferential direction of the trunk part 30; a second part 332 which extends from one end portion of the first part 331 and penetrates the trunk part 30 without passing through a center axis 102 of the trunk part 30 or the outer circumference of the trunk part 30; and a third part 333 which extends from the other end portion of the first part 331 and penetrates the trunk part 30 without passing through the center axis 102 of the trunk part 30 or the outer circumference of the trunk part 30. In the configuration shown, the first part 331 is arcuate in shape. In addition, the second part 332 is a flexed line-like (bent or curved bar-like) in shape. The third part 333 is rectilinear (bar-like) in shape. In addition, the second part 332 and the third part 333 open at the outer circumferential surface of the trunk part 30 to form distal openings (openings) 334 and 335 which each have a circular shape, a tetragonal shape or the like shape.

The first to third parts 331 to 333 are formed at such a position or height as to coincide with the flow channels 201 and 202 of the ports P1 and P2 in the state (hereafter referred to simply as the "cock fitted state") when the cock 3 is fitted in the cock body 2.

That portion of the trunk part 30 which corresponds to the second portion 22 is formed therein with a second flow channel 34 through which the third to sixth ports P3 to P6 formed in the second portion 22 communicate with one another in a predetermined combination.

The second flow channel 34 is so formed that predetermined three ports of the third to sixth ports P3 to P6 can be simultaneously set into an open state or a closed state, and that the turning angle range of the cock 3 for putting the predetermined three ports into a closed state is greater than the turning angle range of the cock 3 for putting the predetermined three ports into an open state.

Specifically, the second flow channel 34 is formed in an X shape. More specifically, the second flow channel 34 includes a first part 341, a second part 342, a third part 343 and a fourth part 344 which extend in radial directions of the trunk part 30 at predetermined angles therebetween and communicate with one another in the vicinity of a central portion of the trunk part 30. In this case, the first part 341, the second part 342, the third part 343 and the fourth part 344 are arranged in this order along a counterclockwise direction. In addition, the first to fourth parts 341 to 344 open at the outer circumferential surface of the trunk part 30, to form distal openings (openings) which each have a circular shape, a tetragonal shape or the like shape. The angle formed between the first part 341 and the second part 342, and the angle formed between the third part 343 and the fourth part 344, are equal to each other, and are each smaller than 90°. On the other hand, the angle formed between the second part 342 and the third part 343, and the angle formed between the fourth part 344 and the second part 342, are equal to each other, and are each greater than 90°. Though the angle formed between the first part 341 and the second part 342 and the angle formed between the third part 343 and the fourth part 344 are each 45° in the configuration shown as an example, the angles are not limited to this value. Also, while the angle formed between the second part 342 and the third part 343 and the angle formed between the fourth part 344 and the first part 341 are each 135° in the configuration shown by way of example, the angles are not limited to this value.

The first to fourth parts 341 to 344 are formed at such a height position as to coincide with the flow channels 203 to 206 in the ports P3 to P6 in the cock fitted state.

In addition, the second flow channel 34 and the first flow channel 33 do not communicate with each other. This helps ensure that the opening/closing of the first port P1 and the second port P2 formed in the first portion 21 and the opening/closing of the third to sixth ports P3 to P6 formed in the second portion 22 can be controlled independently.

As shown in FIG. 5, at the upper side of the trunk part 30, the lever mounting part (operating part mounting part) 31 is provided which is greater than the outside diameter of the trunk part 30 and to which the lever 32 is mounted (fitted). The trunk part 30 and the lever mounting part 31 are preferably formed monolithically. The lever mounting part 31 is in the state of being exposed to the upper side of the hollow cylindrical part 20 in the cock fitted state.

To the lever mounting part 31, the lever 32 being bar-like in shape and extending (protruding) in one direction is mounted so as to protrude radially outward. In the state wherein the lever 32 is mounted to the lever mounting part 31, a turning center portion 322 of the lever 32 and the lever mounting part 31 are fitted to each other. Specifically, the lever 32 would not be turned relative to the lever mounting part 31, and a turning operation of the cock 3 is effected by gripping the lever 32 by fingers and exerting a torque on the lever 32. For this purpose, therefore, both side surfaces of the lever 32 are each formed with a rugged pattern 321 as an example of anti-slipping means.

In addition, in the configuration shown, in the state wherein the lever 32 is mounted to the lever mounting part 31, the protruding direction of the lever 32 is between the protruding direction of the third part 343 and the protruding direction of the fourth part 344, of the second flow channel 34 from the center axis 102.

The cock 3 can be moved, by turning the cock 3, to a priming position for priming before use, a radiopaque material dispensing position for dispensing a radiopaque material into a patient, a physiological saline dispensing position for dispensing physiological saline into the patient, and a blood pressure detection position for detecting the blood pressure of the patient by a pressure sensor.

In this case, the radiopaque material dispensing position, the physiological saline dispensing position and the blood pressure detection position are preferably provided concentratedly within the range of a center angle of not more than 120°, and the priming position is provided outside the range. In the configuration shown by way of example, the radiopaque material dispensing position, the physiological saline dispensing position and the blood pressure detection position are provided concentratedly within the range of a center angle of 45°. That is, the radiopaque material dispensing position, the physiological saline dispensing position and the blood pressure detection position are positioned so that the three positions can be reached through rotational movement of not more than 45°.

As shown in FIG. 5, the cover (seal member) 4 is a member which has a projecting portion at a central portion thereof, and is mounted to the lower end of the hollow cylindrical part 20 of the cock body 2 in such a manner as to seal off the lower end of the lumen 200.

In this case, the projecting portion of the cover 4 is fitted (firmly attached) into a hole in a lower end portion of the trunk part 30. This makes it possible to prevent the trunk part 20 of the cock 3 from being shifted in the direction of the axis 101 relative to the hollow cylindrical part 20 of the cock body 2 or being disengaged.

It is also possible to firmly attach the cover 4 to the hollow cylindrical part 20, not to the trunk part 30.

Materials for forming the cock body 2, the cock 3 and the cover 4 are not limited. Examples of the materials include polyethylene, polypropylene, polybutadiene and the like polyolefins, polyurethane, polystyrene, polymethyl methacrylate and the like acrylic resins, polycarbonate, polyamides, polyethylene terephthalate and the like polyesters, polyacetal, ABS resin, AS resin, ionomers and other fluororesins, and the like resin materials, thermoplastic elastomers based on polyurethane, polyester, polyamide, olefin, styrene or the like, stainless steel, aluminum, titanium and the like metallic materials, and glasses, which may be used either singly or in an arbitrary combination (for example, as a composite material).

In order to secure visibility of the inside of the multi-way cock 1, for example, a light-transmitting material (transparent or translucent material) may be used for forming the cock body 2.

In addition, as shown in FIG. 8, the lever 32 of the multi-way cock 1 is formed, at a position deviated from the turning center portion 322, with a recess 323 opening to the lower side. Inside the recess 323, a pin 324 formed with a flange 326 at an outer circumferential portion thereof is disposed in a vertically movable manner. Between the flange 326 of the pin 324 and an upper portion of the inside of the recess 323, a coil spring 325, representing an example of a biasing means for applying an elastic force, is disposed in a contracted state. The pin 324 is biased downward by an elastic force (restoring force) of the coil spring 325.

Figures 3A, 3B:
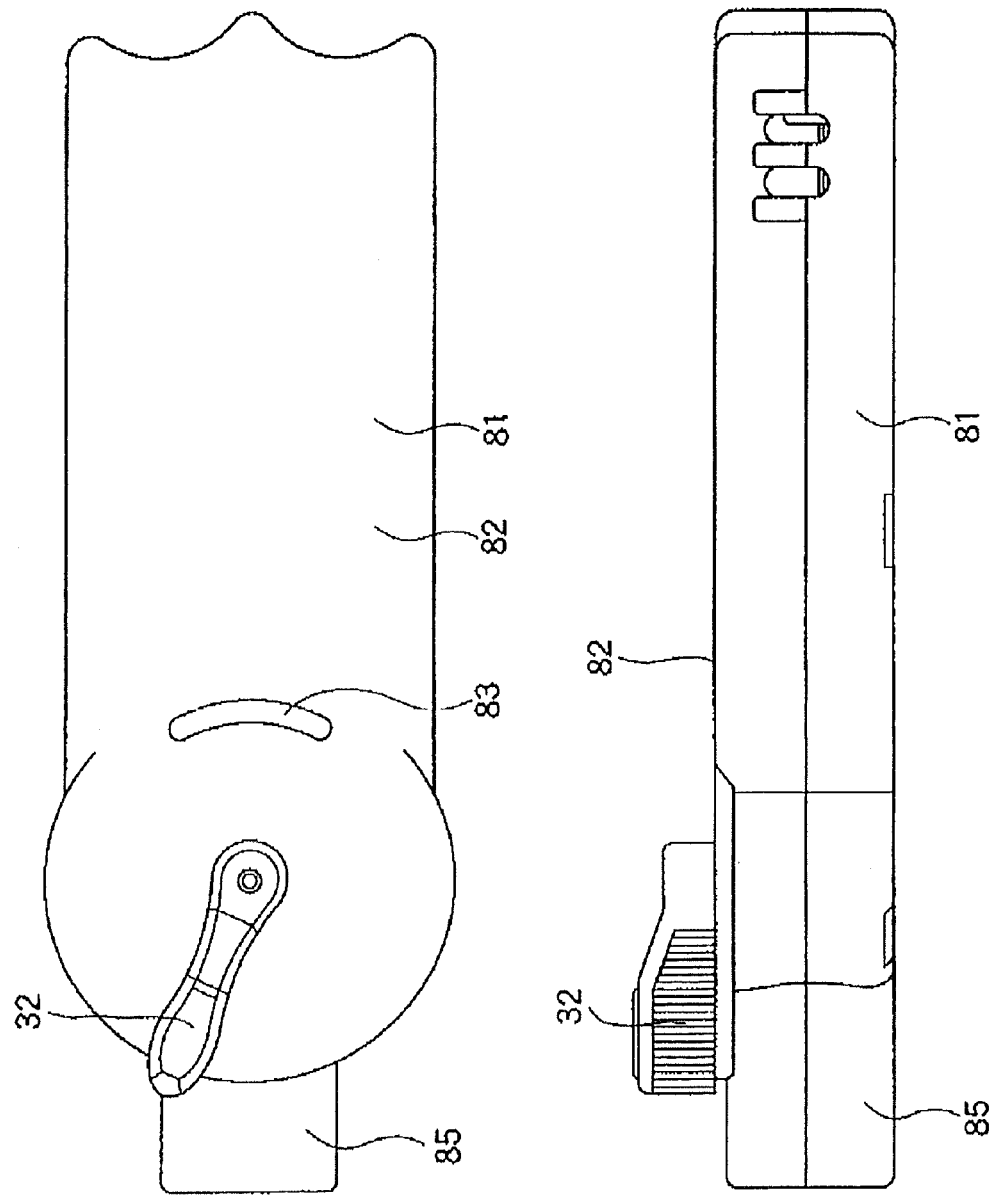
FIG. 3(a) is a plan view of the casing of the liquid dispensing circuit shown in FIG. 1.
FIG. 3(b) is a side view of the casing of the liquid dispensing circuit shown in FIG. 1.
Figure 4:
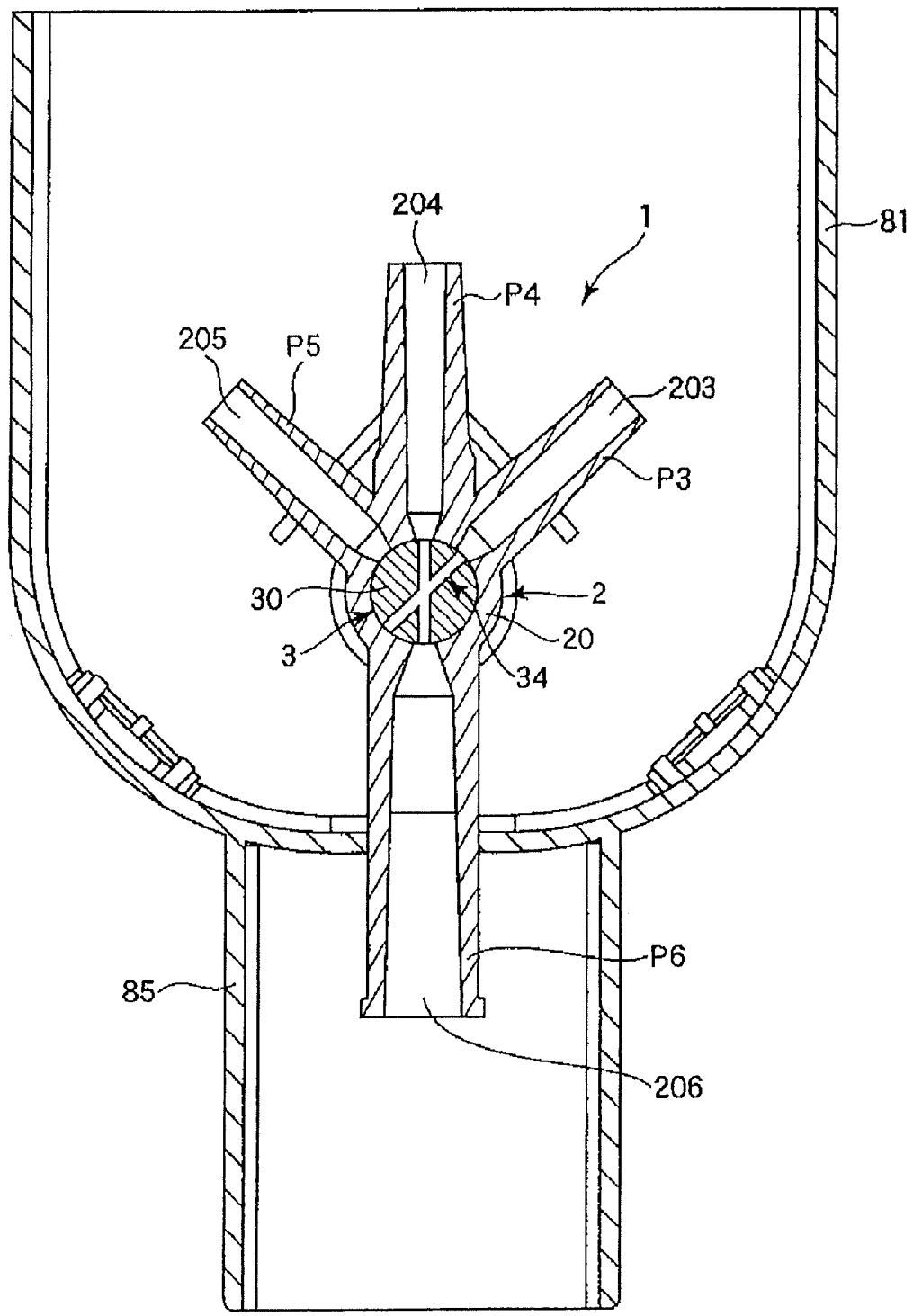
FIG. 4 is a cross-sectional view of the casing of the liquid dispensing circuit shown in FIG. 1.

On the other hand, as shown in FIGS. 1, 3 and 8, an outside surface of the wall portion 82 of the casing 81 includes a groove 83 in the vicinity of the lever 32. The groove 83 extends in an arcuate shape along a circle the center of which coincides with the center of turning (turning center) of the cock 3 and the radius of which is equal to the distance between the turning center of the cock 3 and the pin 324. This helps ensure that when the cock 3 is turned by operating the lever 32 starting from the state shown in FIG. 8(*a*), the pin 324 is moved to a position on the upper side of the groove 83 as shown in FIG. 8(*b*), and the pin 324 moves downward by the biasing force of the coil spring, to be inserted into the groove 83. Once the pin 324 is positioned in the groove 83, the pin 324 will not come out of the groove 83.

Figure 9:
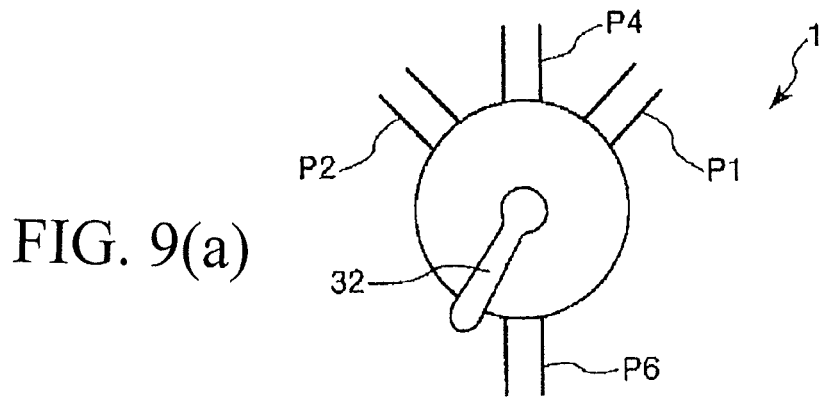
FIGS. 9(a), 9(b) and 9(c) are cross-sectional views somewhat schematically illustrating a flow channel changeover pattern in the multi-way cock shown in FIG. 5.
Figure 9:
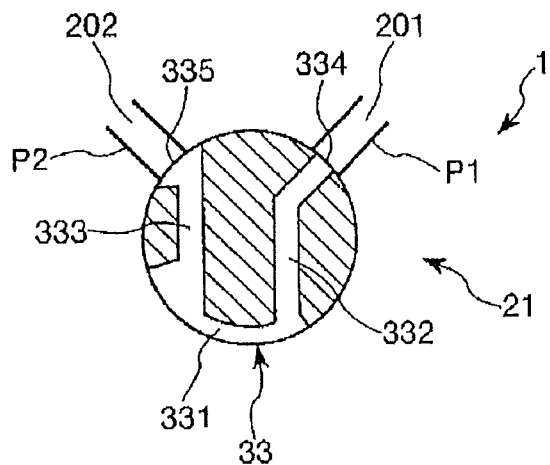
Figure 9:
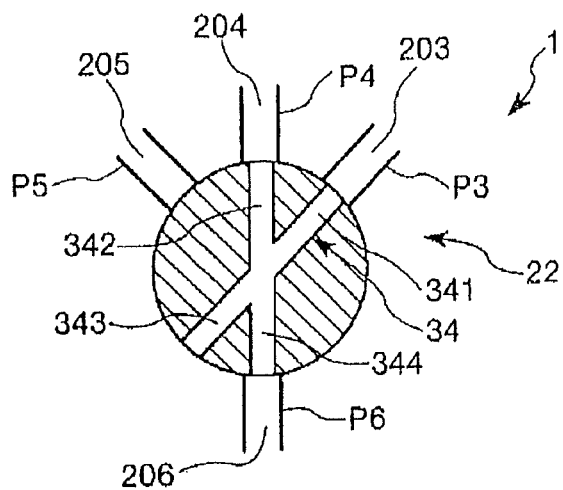

Here, the cock 3 is initially situated in the priming position shown in FIG. 9. The priming position is provided in such a position that the pin 324 is not inserted in the groove 83. As shown in FIG. 9, when the cock 3 is situated in the priming position, the distal opening 334 of the second part 332 of the first flow channel 33 communicates with the first port P1, and the distal opening 335 of the third part 333 communicates with the second port P2, whereby the first port P1 and the second port P2 are set in an open state wherein these ports communicate with each other via the first flow channel 33, whereas the third port P3 and the fourth port P4 and the sixth port P6 are set in an open state wherein these ports communicate with one another via the second flow channel 34.

Then, when the cock 3 is turned by operating the lever 32 as above-mentioned after priming is conducted, the pin 324 is inserted into the groove 83.

When the lever 32 is operated to rotate (turn) the cock 3 clockwise in FIG. 5 relative to the cock body 2, the pin 324 comes into contact (engagement) with an edge portion on one end side of the groove 83, resulting in that the cock 3 cannot be rotated further clockwise in FIG. 5. The position of the cock 3 in this instance is the physiological saline dispensing position, where the positional relationship between the first to sixth ports P1 to P6 of the cock body 2 and the trunk part 30 (the first flow channel 33 and the second flow channel 34) of the cock 3 is as shown in FIG. 11.

Figure 11A:
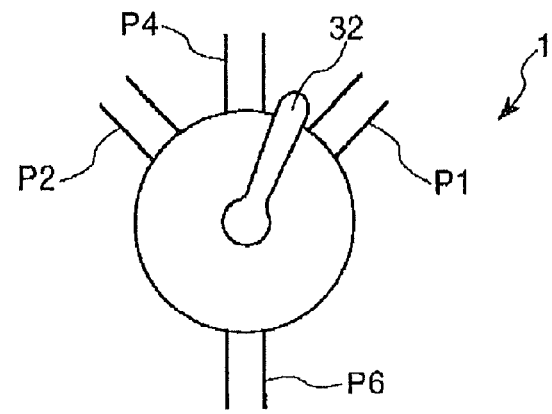
FIGS. 11(a), 11(b) and 11(c) are cross-sectional views somewhat schematically illustrating a flow channel changeover pattern in the multi-way cock shown in FIG. 5.
Figure 11B:
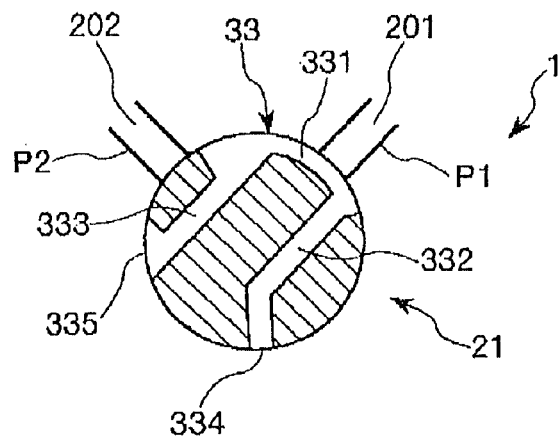
Figure 11C:
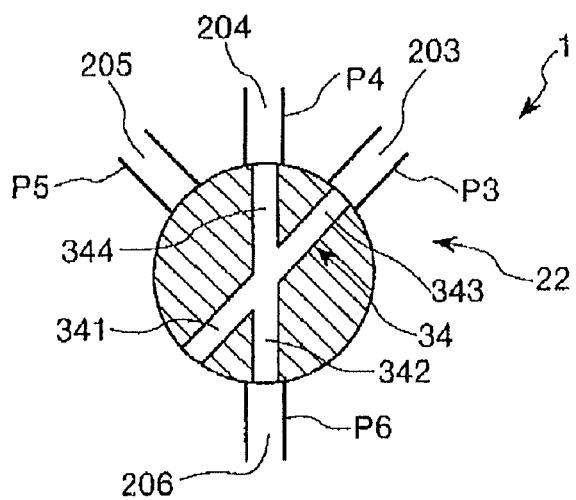

As shown in FIG. 11, when the cock 3 is situated in the physiological saline dispensing position, the first port P1 and the second port P2 are each set in a closed state, whereas the third port P3 and the fourth port P4 and the sixth port P6 are set in an open state in which these ports communicate with one another via the second flow channel 34.

In addition, when the cock 3 is rotated (in the configuration shown, rotated by 45°) counterclockwise in FIG. 5 relative to the cock body 2 from the physiological saline dispensing position, the pin 324 comes into contact with an edge portion on the other end side of the groove 83, resulting in that the cock 3 cannot be rotated further counterclockwise in FIG. 5. The position of the cock 3 in this instance is the radiopaque material dispensing position, where the positional relationship between the first to sixth ports P1 to P6 of the cock body 2 and the trunk part 30 (the first flow channel 33 and the second flow channel 34) of the cock 3 is as shown in FIG. 10.

Figure 10A:
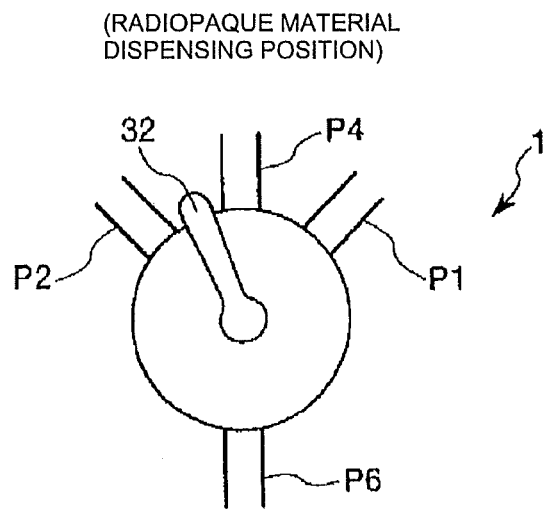
FIG. 10 is a cross-sectional view somewhat schematically illustrating a flow channel changeover pattern in the multi-way cock shown in FIG. 5.
Figure 10B:
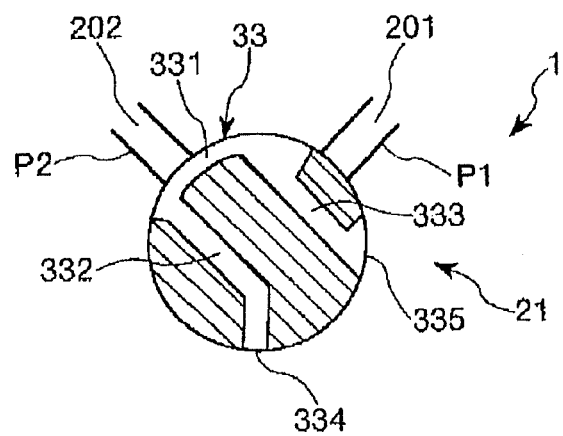
Figure 10C:
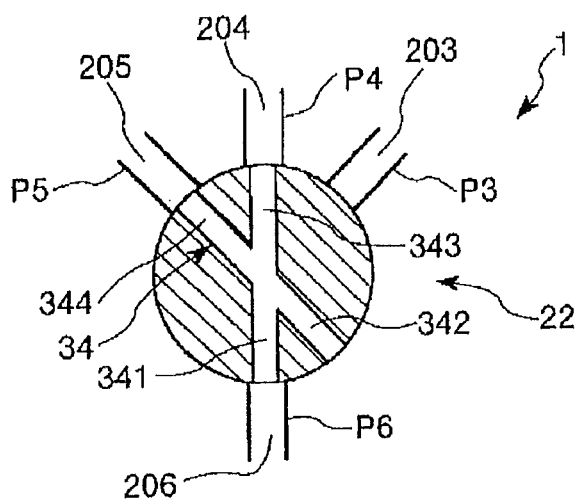

As shown in FIG. 10, when the cock 3 is situated in the radiopaque material dispensing position, the first port P1 and the second port P2 are each set in a closed state, whereas the fourth port 4 and the fifth port P5 and the sixth port P6 are set in an open state in which these ports communicate with one another via the second flow channel 34.

The time when the cock 3 is situated between the radiopaque material dispensing position and the physiological saline dispensing position as shown in FIG. 12 is the time when the cock 3 is situated in the blood pressure detection position. As shown in FIG. 12, when the cock 3 is situated in the blood pressure detection position, the first part 331 of the first flow channel 33 communicates with each of the first port P1 and the second port P2, whereby the first port P1 and the second port P2 are set in an open state in which these ports communicate with each other via the first flow channel 33, whereas the third port P3, the fourth port P4, the fifth port P5 and the sixth port P6 are each set in a closed state.

Thus, by virtue of the configuration of the pin 324 and the groove 83, the turning range of the cock 3 relative to the hollow cylindrical part 20 is restrained within such a range that the cock 3 can be moved into the radiopaque material dispensing position, the physiological saline dispensing position and the blood pressure detection position. In addition, by virtue of the configuration of the pin 324 and the groove 83, the cock 3 is positionable in each of the radiopaque material dispensing position and the physiological saline dispensing position. After the pin 324 is inserted into the groove 83, the pin 324 and the groove 83 prevent the cock 3 from being moved into the priming position. In other words, once the cock 3 is moved from a first region in which the priming position is provided into a second region in which the radiopaque material dispensing position, the physiological saline dispensing position and the blood pressure detection position are provided, the cock 3 cannot be returned to the first region.

The pin 324 and the groove 83 constitute an example of a positioning means for restricting the turning range of the cock 3 relative to the hollow cylindrical part 20. When the positioning means is not functioning, in other words when the pin 324 is not inserted in the groove 83, the cock 3 can be moved into the priming position.

The upper surface of the wall portion 82 of the casing 81 is preferably provided with indicators respectively indicating the priming position, the radiopaque material dispensing position, the physiological saline dispensing position and the blood pressure detection position. This makes it possible to move the cock 3 into a target position assuredly.

Now, operations of (a method of using) the liquid dispensing circuit 10 will be described below referring to FIGS. 2 and 9 to 12.

First, priming is conducted. At the time of priming, the lever 32 is operated to move the cock 3 into the priming position shown in FIG. 9. This results in that, as above-mentioned, the distal opening 334 of the second part 332 of the first flow channel 33 communicates with the first port P1, and the distal opening 335 of the third part 333 communicates with the second port P2, whereby the first port P1 and the second port P2 are set in an open state in which these ports communicate with each other via the first flow channel 33, whereas the third port P3 and the fourth port P4 and the sixth port P6 are set in an open state in which these ports communicate with one another via the second flow channel 34.

Next, a pusher 111 in the syringe 11 is moved toward the proximal end. This results in the physiological saline in the container being introduced into the syringe 11 via the bottle needle 75, the tube 64, the check valve 71, the tube 63, the third port P3, the second flow channel 34 and the sixth port P6. Subsequently, the pusher 111 in the syringe 11 is moved toward the distal end (in the distal direction). This causes the physiological saline in the syringe 11 to flow through the sixth port P6, the second flow channel 34, the fourth port P4, the check valve 72, the branched connector 77, the tube 65, the three-way cock 74 and the tube 66, and to flow out via the distal end of the tube 66. In addition, the physiological saline flows from the branched connector 77 through the tube 61, the first port P1, the first flow channel 33, the second port P2 and the tube 62, to flow out via the distal end of the tube 62. As a result, each of the just-mentioned portions is primed.

Next, the lever 32 is operated to move the cock 3 into the radiopaque material dispensing position shown in FIG. 10. This results in, as above-mentioned, the first port P1 and the second port P2 are each set in a closed state, whereas the fourth port P4 and the fifth port P5 and the sixth port P6 are set in an open state in which these ports communicate with one another via the second flow channel 34.

Subsequently, the pusher 111 in the syringe 11 is moved toward the proximal end. This causes the radiopaque material in the container containing the radiopaque material to be introduced into the syringe 11 via the bottle needle 76, the tube 68, the check valve 73, the tube 67, the fifth port P5, the second flow channel 34 and the sixth port P6.

Next, the pusher 111 in the syringe 11 is moved toward the distal end. This causes the radiopaque material in the syringe 11 to flow through the sixth port P6, the second flow channel 34, the fourth port P4, the check valve 72, the branched connector 77, the tube 65, the three-way cock 74 and the tube 66, and to flow out via the distal end of the tube 66. As a result, each of the just-mentioned portions can be primed. By these operations, priming of the liquid dispensing circuit 10 is completed, followed by a predetermined procedure. The description of the predetermined procedure is omitted.

In the case of dispensing the radiopaque material into a patient, the lever 32 is operated to move the cock 3 into the radiopaque dispensing position shown in FIG. 10. This ensures that, as above-mentioned, the first port P1 and the second port P2 are each set in a closed state, whereas the fourth port P4 and the fifth port P5 and the sixth port P6 are set in an open state in which these ports communicate with one another via the second flow channel 34. As a result, the patient's artery and the pressure sensor are disconnected from each other.

Next, the pusher 111 in the syringe 11 is moved toward the proximal end. This causes the radiopaque material in the container to be introduced into the syringe 11 via the bottle needle 76, the tube 68, the check valve 73, the tube 67, the fifth port P5, the second flow channel 34 and the sixth port P6. In this case, by the action of the check valve 72, the patient's blood is inhibited from flowing to the syringe 11 side.

Subsequently, the pusher 111 in the syringe 11 is moved toward the distal end. This causes the radiopaque material in the syringe 11 to flow out via the sixth port P6, the second flow channel 34, the fourth port P4, the check valve 72, the branched connector 77, the tube 65, the three-way cock 74, the tube 66 and a catheter connected to the tube 66, into the vicinity of a stenosed part of the patient's coronary artery.

After the cock 3 is thus situated in the first position, the radiopaque material can be continuously sucked in and discharged by only operating the syringe 11, without having to operate the lever 32.

To dispense the physiological saline into the patient, the lever 32 is operated to move the cock 3 into the physiological saline dispensing position shown in FIG. 11. This ensures that, as above-mentioned, the first port P1 and the second port P2 are each set in a closed state, whereas the third port P3 and the fourth port P4 and the sixth port P6 are set in an open state wherein these ports communicate with one another via the second flow channel 34. This results in a state in which the patient's artery and the pressure sensor are disconnected from each other.

Next, the pusher 111 in the syringe 11 is moved toward the proximal end. This causes the physiological saline in the container (i.e., the container containing physiological saline) to be introduced into the syringe 11 via the bottle needle 75, the tube 64, the check calve 71, the tube 63, the third port P3, the second flow channel 34 and the sixth port P6. In this case, by the action of the check valve 72, the patient's blood is inhibited from flowing to the syringe 11 side.

Subsequently, the pusher 111 in the syringe 11 is moved toward the distal end. This causes the physiological saline in the syringe 11 to flow out through the sixth port P6, the second flow channel 34, the fourth port P4, the check valve 72, the branched connector 77, the tube 65, the three-way cock 74, the tube 66 and a catheter (not shown) connected to the tube 66, into the vicinity of the stenosed part of the patient's coronary artery.

After the cock 3 is thus situated in the second position, the physiological saline can be continuously sucked in and discharged by only operating the syringe 11, without having to operate the lever 32.

In addition, to measure the artery pressure (the blood pressure in the coronary artery) of the patient and display the measurement result on a monitor, the lever 32 is operated to move the cock 3 into the blood pressure detection position shown in FIG. 12. This ensures that, as above-mentioned, the first part 331 of the first flow channel 33 communicates with each of the first port P1 and the second port P2, whereby the first port P1 and the second port P2 are set in an open state wherein these ports communicate with each other via the first flow channel 33, whereas the third port P3, the fourth port P4, the fifth port P5 and the sixth port P6 are each set in a closed state. This results in a state in which the patient's artery and the pressure sensor are connected with each other, and the patient's artery pressure is measured by the pressure sensor through the catheter, the tube 66, the three-way cock 74, the tube 65, the branched connector 77, the tube 61, the first port P1, the first flow channel 33, the second port P2 and the tube 62, the measurement result being displayed on the monitor.

As has been described above, the liquid dispensing circuit 10 is configured so that by only turning the single lever 32 (cock 3), it is possible to freely select the opening/closing of the first to sixth ports P1 to P6, and to relatively easily and swiftly perform complicated flow channel changing-over operations.

To be more specific, when the cock 3 is situated in the priming position, priming can be securely carried out by only operating the syringe 11. In addition, when the cock 3 is situated in the radiopaque material dispensing position, the radiopaque material can continuously be sucked in and discharged by only operating the syringe 11, without operating the lever 32. When the cock 3 is situated in the physiological saline dispensing position, the physiological saline can be continuously sucked in and discharged by only operating the syringe 11, without operating the lever 32. Furthermore, when the cock 3 is situated in the blood pressure detection position, the patient's artery pressure can be measured and displayed on the monitor.

In addition, since the first portion 21 and the second portion 22 are provided side by side along the axis 101 of the hollow cylindrical part 20, downsizing of the multi-way cock 1 can be achieved.

While the liquid dispensing circuit disclosed here has been described above based on the embodiment shown in the drawings as one example, the invention is not to be restricted to the above embodiment, and the configuration of each part can be replaced by a part having a different configuration exhibiting the same or similar function. Other features can also be added.

The number of ports provided at the outer circumference of the first portion of the tubular part of the cock body is not limited to two, but may be three or more.

In addition, the number of ports provided at the outer circumference of the second portion of the tubular part of the cock body is not limited to four but may be five or more.

The number of portions of the tubular part of the cock body which are provided with the ports is not limited to two (the first portion and the second portion) but may be three or more. Similarly, the number of the flow channels formed in the trunk part of the cock is not limited to two (the first flow channel and the second flow channel) but may be three or more.

In other words, a configuration may be adopted in which the tubular part of the cock body further has a third portion provided at the outer circumference thereof with at least two ports, the trunk part of the cock is formed further with a third flow channel through which the ports provided in the third portion communicate with one another in a predetermined combination, and the opening/closing of the ports provided in the first portion, the second portion and the third portion is selected by turning the cock. In this case, the third portion is preferably provided in a line with the first portion and the second portion along the axis (center axis) of the tubular part. In addition, the third flow channel preferably communicates with neither the first flow channel nor the second flow channel.

An operating part for turning the cock is not restricted to the above-described lever. For example, the operating part may be a part extending in two or more directions, a handle, a dial or the like.

In addition, the use of the liquid dispensing circuit disclosed here is not limited. The liquid dispensing circuit is applicable not only to the above-described embodiment but also to the cases where a multiplicity of tubes is used, such as, for example, an anesthetic procedure.

As mentioned above, priming operation before use of the liquid dispensing circuit can be carried out rather easily and assuredly, and complicated flow channel changing-over operations during use of the liquid dispensing circuit can be carried out quite easily and swiftly.

The tubular part of the cock body of the multi-way cock has the first portion and the second portion provided with groups of ports, and the cock for selecting the communicating/non-communicating (open/closed) states of these ports is a common (single) cock, and, therefore, complicated flow channel changing-over operations can be carried out easily and speedily.

In addition, when the cock is situated in the priming position, the first port and the second port are set in an open state wherein these ports communicate with each other via the first flow channel, whereas the third port and the fourth port and the sixth port are set in an open state wherein these ports communicate with one another via the second flow channel. In this state, therefore, physiological saline can be fed to the liquid feeding means side via the third line, the third port, the second flow channel and the sixth port by the liquid feeding means, for reserving the physiological saline on the side. This enables priming of the third line, the third port, the second flow channel and the sixth port. Then, by the liquid feeding means, the physiological saline can be fed from the sixth port to the second flow channel, the fourth port and the fourth line, whereby priming of the second flow channel, the fourth port and the fourth line can be achieved. In addition, since the physiological saline fed by the liquid feeding means is fed also from the fourth line into the first line, the physiological saline is fed to the first line, the first port, the first flow channel, the second port and the second line, whereby priming of the first line, the first port, the first flow channel, the second port and the second line can be achieved. Because the first portion and the second portion of the multi-way cock are provided in a line along the axis of the tubular part, downsizing of the multi-way cock can be ensured.

The detailed description above describes features and aspects of an embodiment of a liquid dispensing circuit disclosed by way of example. The invention is not limited, however, to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A liquid dispensing circuit comprising:

a multi-way cock comprised of a tubular cock body and a trunk part, the tubular cock body possessing a lumen, the trunk part being rotatably positioned in the lumen of the tubular cock body to rotate at least from a first rotational position to a second rotational position, the first position being different from the second position;

the tubular cock body including opposite axial ends and a circumferential outer surface between the axial ends, the tubular cock body including a plurality of ports projecting outwardly away from the circumferential outer surface of the tubular cock body, the plurality of ports comprising a first port, a second port, a third port, a fourth port, a fifth port and a sixth port;

the first port and the second port each possessing a lumen having one end opening to the lumen in the tubular cock body and an opposite end opening outside the tubular cock body;

the third port, the fourth port, the fifth port and the sixth port each possessing a lumen having one end opening to the lumen in the tubular cock body and an opposite end opening outside the tubular cock body;

the trunk part including a first flow channel configured so that in the first rotational position of the trunk part, one portion of the first flow channel opens to the one end of the first port while an other portion of the first flow channel opens to the one end of the second port so that the first and second ports fluidly communicate with one another by way of the first flow channel, and so that in the second rotational position of the trunk part, the other portion of the first flow channel is spaced from the one end of the second port, and the first and second ports are not in fluid communication with one another by way of the first flow channel;

the one portion of the first flow channel and the other portion of the first flow channel being circumferentially spaced from one another;

the trunk part also including a second flow channel separate from the first flow channel and axially spaced from the first flow channel, the second flow channel being configured so that: in the second rotational position of the trunk part, a first portion of the second flow channel opens to the one end of the third port, a second portion of the second flow channel opens to the one end of the fourth port and a third portion of the second flow channel opens to the one end of the sixth port so that the third, fourth and sixth ports fluidly communicate with one another by way of the second flow channel; in the first rotational position of the trunk part, the first portion of the second flow channel opens to the one end of the third port, the second portion of the second flow channel opens to the one end of the fourth port and the third portion of the second flow channel opens to the one end of the sixth port so that the third, fourth and sixth ports fluidly communicate with one another by way of the second flow channel;

the first portion of the second flow channel, the second portion of the second flow channel and the third portion of the second flow channel being circumferentially spaced from one another;

a plurality of tubes each possessing a lumen and connected to a different one of the plurality of ports so that the lumen in each tube is in fluid communication with the respective port; and the plurality of tubes including one tube connected to both the third port and a source of saline to communicate the third port with the source of saline, an other tube connected to both the fifth port and a source of radiopaque material to communicate the fifth port with the source of radiopaque material, and a further tube connected to both the sixth port and a syringe to communicate the sixth port with the syringe.

2. The liquid dispensing circuit according to claim 1, wherein the first port possesses an axis and the second port possesses an axis, the axis of the first port and the axis of the second port lying in a common plane.

3. The liquid dispensing circuit according to claim 1, wherein the third port possesses an axis, the fourth port possesses an axis, the fifth port possesses an axis and the sixth port possesses an axis, the axes of the third port, the fourth port, the fifth port and the sixth port lying in a common plane.

4. The liquid dispensing circuit according to claim 1, wherein each of the lines possesses a distal end portion, and including a needle positioned at the distal end portion of two of the lines.

5. The liquid dispensing circuit according to claim 1, wherein the plurality of tubes includes: a tube possessing one end portion connected to the first port and an opposite end portion connected to a branched connector; and an additional tube possessing one end portion connected to the second port and an opposite end portion connected to blood pressure detection means for detecting blood pressure of a patient.

6. The liquid dispensing circuit according to claim 1, wherein the trunk part is rotatable to a third position different from the first and second positions, the first flow channel possessing a third part which opens to the first port when the trunk part is in the third position and also possessing a fourth part which opens to the second port when the trunk part is in the third position so that the first and second ports are in fluid communication with one another by way of the first flow channel when the trunk part is in the third position, the third part and the fourth part of the first flow channel being different from the first and second parts of the first flow channel.

7. The liquid dispensing circuit according to claim 6, wherein the second flow channel is configured so that the third port, the fourth port, the fifth port and the sixth port are not in fluid communication with one another by way of the second flow channel when the trunk part is in the third position, and also possessing a fourth part which opens to the second port when the trunk part is in the third position so that the first and second ports are in fluid communication with one another by way of the first flow channel when the trunk part is in the third position.

8. A liquid dispensing circuit comprising:
a multi-way cock comprised of a cock body having a tubular part, the tubular part of the cock body including axially side-by-side first and second portions which each possess an outer circumference;
the first portion of the cock body including a first port and a second port both positioned at the outer circumference of the first portion in circumferentially side-by-side relation;
the second portion of the cock body including a third port, a fourth port, a fifth port, and a sixth port sequentially positioned side-by-side about the outer circumference of the second portion;
the cock also including a trunk part turnably positioned in the tubular part, the trunk part being provided with a first flow channel to communicate the first port and the second port, the trunk part also being provided with a second flow channel to communicate different combinations of the third port, the fourth port, the fifth port and the sixth port in;
a second line having one end portion connected to the second port and an opposite end portion configured to be connected to blood pressure detection means for detecting blood pressure of a patient;
a third line having one end portion connected to the third port and an opposite end portion connected to a container containing physiological saline;
a fourth line having one end portion connected to the fourth port and an opposite end portion configured to be connected to a flow channel communicating with a blood vessel of the patient;
a first line connecting the first port and the fourth line;
a fifth line having one end portion connected to the fifth port and an opposite end portion connected to a container containing a radiopaque material;
wherein the sixth port is connected to a syringe for feeding a liquid from one of the first line, the second line, the third line, the fourth line and the fifth line to a different one of the first line, the second line, the third line, the fourth line and the fifth line through the multi-way cock;
the cock being movable to shift between a priming position to prime portions of the circuit, a radiopaque material dispensing position to dispense the radiopaque material to the patient, a physiological saline dispensing position to dispense the physiological saline to the patient, and a blood pressure detection position to detect the blood pressure of the patient by the pressure detection means; and
when the cock is situated in the priming position, the first port and the second port communicate with each other through the first flow channel, while at the same time the third port, the fourth port and the sixth port communicate with one another through the second flow channel.

9. The liquid dispensing circuit according to claim 8, wherein when the cock is in the blood pressure detection position, the first port and the second port communicate with each other through the first flow channel, whereas the third port, the fourth port, the fifth port and the sixth port do not communicate with one another.

10. The liquid dispensing circuit according to claim 8, wherein when the cock is in the radiopaque material dispensing position, the first port and the second port do not communicate with one another, whereas the fourth port, the fifth port and the sixth port each communicate with each other through the second flow channel.

11. The liquid dispensing circuit according to claim 8, wherein when the cock is in the physiological saline dispensing position, the first port and the second port do not communicate with one another, whereas the third port, the fourth port and the sixth port each communicate with each other through the second flow channel.

12. The liquid dispensing circuit according to claim 8, wherein the radiopaque material dispensing position, the physiological saline dispensing position and the blood pressure detection position are provided within a range of not more than 120°, and the priming position is outside the range.

13. The liquid dispensing circuit according to claim 8, wherein the first flow channel includes: a first part provided in an outer circumferential surface of the trunk part and extending circumferentially along the trunk part, the first part possessing one end portion and an other end portion; a second part extending from the one end portion of the first part, penetrating into the trunk part and forming a distal opening at the outer circumferential surface of the trunk part, the distal opening being spaced from the first part; and a third part extending from the other end portion of the first part, penetrating the trunk part and forming a distal opening at the outer circumferential surface of the trunk part that is spaced from the distal opening of the second part.

14. The liquid dispensing circuit according to claim 13, wherein when the cock is in the priming position, the distal opening of the second part communicates with the first port, and the distal opening of the third part communicates with the second port, whereby the first port and the second port communicate with each other through the first flow channel.

15. The liquid dispensing circuit according to claim 13, wherein when the cock is in the blood pressure detection position, the first part communicates with both the first port and the second port so that the first port and the second port communicate with each other through the first flow channel, whereas the third port, the fourth port, the fifth port and the sixth port are each set in a closed state in which the third port, the fourth port, the fifth port and the sixth port do not communicate with one another.

16. A liquid dispensing circuit comprising:
a multi-way cock comprised of a cock body possessing a tubular part, the tubular part of the cock body including axially side-by-side first and second portions which each possess an outer circumference;
the first portion of the cock body including a first port and a second port both positioned at the outer circumference of the first portion in circumferentially side-by-side relation;
the second portion of the cock body including a third port, a fourth port, a fifth port, and a sixth port sequentially positioned side-by-side about the outer circumference of the second portion;
the cock also including a trunk part turnably positioned in the tubular part, the trunk part being provided with a first flow channel to communicate the first port and the second port, the trunk part also being provided with a second flow channel to communicate the third port, the fourth port, the fifth port and the sixth port;
a second line possessing one end portion connected to the second port and an opposite end portion configured to be connected to blood pressure detection means for detecting blood pressure of a patient;

a third line possessing one end portion connected to the third port and an opposite end portion configured to be connected to a container containing physiological saline;

a fourth line possessing one end portion connected to the fourth port and an opposite end portion configured to be connected to a flow channel communicating with a blood vessel of the patient;

a first line connecting the first port and the fourth line;

a fifth line possessing one end portion connected to the fifth port and an opposite end portion configured to be connected to a container containing a radiopaque material;

wherein the sixth port is configured to be connected to liquid feeding means for feeding a liquid from one of the first line, the second line, the third line, the fourth line and the fifth line to a different one of the first line, the second line, the third line, the fourth line and the fifth line through the multi-way cock;

the cock being movable to shift from a priming position, a radiopaque material dispensing position to dispense the radiopaque material to the patient, a physiological saline dispensing position to dispense the physiological saline to the patient, and a blood pressure detection position to detect the blood pressure of the patient by the pressure detection means;

when the cock is situated in the priming position, the first port and the second port communicate with each other through the first flow channel, while at the same time the third port, the fourth port and the sixth port communicate with one another through the second flow channel;

a first engagement part operatively connected to the trunk part so that rotation of the trunk part results in rotation of the first engagement part;

the first engagement part being out of engagement with a second engagement part when the cock is in the priming position; and the first engagement part engaging the second engagement part when the cock is in the radiopaque material dispensing position, the physiological saline dispensing position and the blood pressure detection position, the engagement of the first engagement part and the second engagement part when the cock is in the radiopaque material dispensing position, the physiological saline dispensing position and the blood pressure detection position preventing the cock from being moved to the priming position.

17. The liquid dispensing circuit according to claim 16, wherein the first engagement part is a pin and the second engagement part is a groove.

* * * * *